United States Patent [19]

Sellers

[11] 3,986,111
[45] Oct. 12, 1976

[54] INVERTED VOLTAGE GERDIEN CONDENSER

[75] Inventor: Bach Sellers, Sudbury, Md.

[73] Assignee: The United States of America as represented by the Secretary of the Navy, Washington, D.C.

[22] Filed: Dec. 24, 1974

[21] Appl. No.: 536,076

[52] U.S. Cl. .......................... 324/71 R; 324/71 CP; 250/282; 250/287; 324/33; 73/194 F
[51] Int. Cl.² ...................... G01N 27/62; H01J 39/34
[58] Field of Search ............... 324/71 R, 71 PC, 33; 313/230; 73/194 F; 250/282, 287, 286

[56] References Cited
UNITED STATES PATENTS

| | | | |
|---|---|---|---|
| 2,637,208 | 5/1953 | Mellen | 73/194 |
| 2,721,972 | 10/1955 | Rothstein | 324/33 |
| 2,946,887 | 7/1960 | Castle, Jr. | 250/41.9 |
| 2,950,387 | 8/1960 | Brubaker | 250/286 |
| 3,699,333 | 10/1972 | Cohen et al. | 250/41.9 TF |
| 3,827,217 | 8/1974 | Volsy | 55/121 |

OTHER PUBLICATIONS
Beweglichkeitsspektrometrie Atmospharischer Ionen, J. Eichmeier und., W. Braun, Meteorol, Radsch., 25, J. G. Heft, 1972.

Primary Examiner—R. V. Rolinec
Assistant Examiner—Vincent J. Sunderdick
Attorney, Agent, or Firm—R. Sciascia; R. Beers; S. Sheinbein

[57] ABSTRACT

A "Gerdien Condenser" spectrometer for use in a moving air environment for measuring ion densities wherein a constant, electric field is provided in the direction opposite to prior art devices so that the outer cylindrical electrode of the condenser functions as the ion collector. This functional change for the outer electrode permits the use of a small-radius annular opening with a larger width as the entrance for the ions to be measured. This change in the shape of the entrance to the condenser chamber substantially reduces the gas turbulence within the chamber thus increasing the ion density measurement accuracy. The outer electrode may be segmented to further increase the ion measurment accuracy.

6 Claims, 2 Drawing Figures

INVERTED VOLTAGE GERDIEN CONDENSER

BACKGROUND OF THE INVENTION

1. Field of Invention

The present invention relates to atmospheric testing instruments and in particular to ion spectrometers.

2. Discussion of the Prior Art

It is well known that the interaction of air molecules with energy radiation produces various, charged, ionic species. Ultraviolet radiation from the sun and radioactive radiation from the bombs and reactors are examples of such ion-producing, energy radiation.

It is clearly desirable to be able to take accurate, ion-density measurements to facilitate, for example, an investigation of the interaction of solar energy with the atmosphere, or to facilitate the measurement of nuclear bomb radiation or nuclear reactor leakage.

Various devices and methods have been adopted in the prior art to measure this basic, physical, atmospheric parameter (ion density). These devices and methods are generally based around a device called a "Gerdien Condenser." The operation of the "Gerdien Condenser" is in turn based on the fact that each ion has a different mobility factor K which is dependent on the chemical nature of the ion, and the fact that the drift velocity V of each ion is related to this mobility by the equation $V = KE$ where $E$ is the electric field. In a time-independent, electric field the distance traveled by an ion in a time $t$ depends only upon its mobility $K$. Thus, this ion-mobility individuality may be used to effect a separation of the various charged ions present.

A "Gerdien Condenser" consists of a small-radius, cylindrical electrode and a large-radius, cylindrical electrode concentrically located with respect to each other and with a potential difference between them. The atmosphere or gas to be tested is passed through an annular ring located in the nose of the spectrometer, which covers the opening between the two, concentric cylinders. The center electrode is designated as the collector electrode and the system is set up accordingly. Thus the annular ring in the nose is placed relatively close to the outer, cylindrical electrode and the electrical potential on the center electrode is made opposite in polarity to the charge of the ion that it is desired to measure. Thus, upon the entrance of the ions through the annular ring, an ion trajectory is set up from the larger annular ring to the small-radius cylindrical electrode. The ions intersect with the center electrode at different points depending upon their velocity which, in turn, is dependent on the individual mobilities.

A major problem with this design is that when this instrument is carried by such upper atmosphere vehicles as rockets, airplanes, and balloons, a very high air or gas turbulence is generated within the chamber between the concentric cylinders. This air turbulence has a substantial effect on the ion-measurement accuracy.

SUMMARY OF THE INVENTION

Briefly, a low-complexity spectrometer is provided which alleviates the turbulence and accuracy problems of the prior art by using concentric electrodes with their potentials inverted relative to the prior art designs. The system comprises a small-radius, cyclindrical, center electrode and a large-radius, cylindrical, outer electrode located concentrically around the center electrode. The outer electrode functions as the ion collector and is given an ion-attracting potential in accordance with this function. The outer electrode is also segmented to provide for an accurate analysis of the ion densities on the electrode. A nose containing an annular ring covers one end of the outer electrode.

Due to this inversion of electrode functions (the outer electrode now acting as the ion collector), the annular ring in the nose may be given a small radius and a wider width thus substantially cutting down the turbulence of the air in the chamber between the concentric electrodes.

OBJECTS OF THE INVENTION

An object of the present invention is to increase the accuracy of ion spectrometers.

A further object is to decrease the turbulence in a "Gerdien Condenser" spectrometer.

Other objects, advantages, and novel features of the present invention will become apparent from the following detailed description of the invention when considered in conjunction with the accompanying drawings.

DETAILED DESCRIPTION OF THE INVENTION

Figure 1:
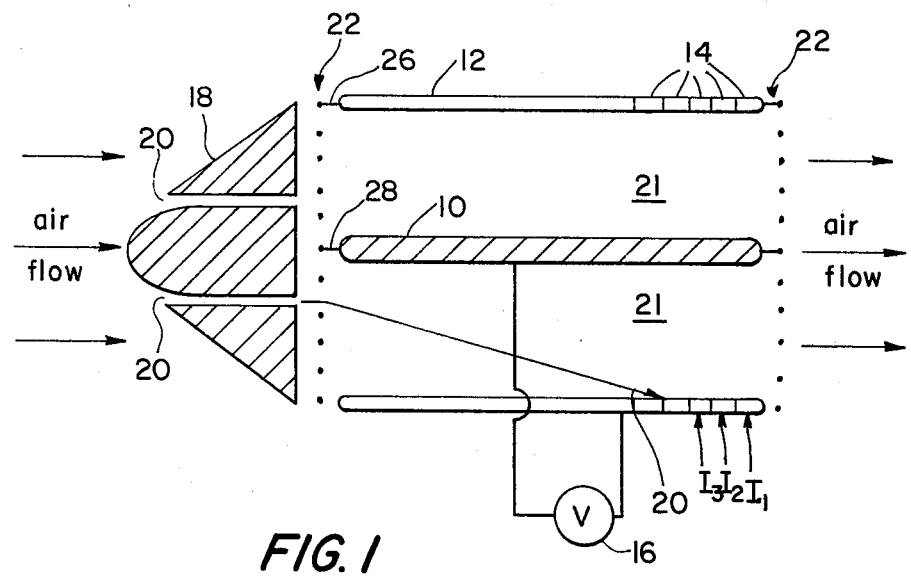
FIG. 1 is a cross-sectional view of one embodiment of the ion spectrometer of the present invention.

Referring to the drawings, FIG. 1 presents a schematic diagram of the basic "Gerdien Condenser" modified as taught by the present invention. The small-radius, cylindrical, center conductor 10 and the large-radius, cylindrical outer conductor 12 form an open-ended, cylindrical chamber 21. A covering piece 18 with an annular opening 20 is placed at one end of the cylindrical chamber 21 to permit gas entrance into the chamber 21 through the annular opening 20. Thus, when the condenser is located in a moving vehicle such as a rocket, aircraft, or balloon, and has only its covering nose 18 exposed to the environment outside the moving vehicle, then an air current is set up through the annular opening 20 in the direction shown in the figure. It should be understood that this type of condenser is not restricted to moving vehicles, but may be utilized in any moving-air environment such as, for example, a stationary system where air is drawn through the annular openings 20 with a fan.

A d.c. voltage supply 16 is placed across the two cylindrical electrodes 10 and 12 as shown in order to set-up an electric field between the two electrodes. When the air current flowing through the annular opening 20 contains charged particles (i.e., ions), these particles are attracted to one or the other of the electrodes 10 and 12 depending on their charges. The current distribution measured along the length of the electrodes may be taken in order to deduce the mobility spectrum of the charged particles present in the air.

As mentioned above, prior art devices used the center electrode 10 as the charged particle or ion collector and thus took the current measurements from this electrode. In order to make this feasible, the polarity of the center electrode 10 (determined by the connection of the power supply 16) must be set so that it attracts the charged particles that it is desired to measure. A second requirement is that there be a sufficient distance radially between the center electrode 10 and the annular opening 20 so that a proper current distribution may be obtained over the length of the electrode 10. Thus, prior art condensers have annular nose openings 20 with large radii relative to the center-electrode radii. But since the volume of air flowing through the condenser chamber must be restricted in order to obtain valid current measurements, such large circumference openings must have very small annular widths. (The size of the annular opening is a function of the velocity of the vehicle where the device is attached to a moving vehicle.) This restriction to a small, annular width opening creates a high degree of gas turbulence within the condenser chamber. Such high gas turbulence tends to make any current distribution readings inaccurate.

The present invention obviates this turbulence problem by reversing the polarities of the electrodes from the normal mode so that the outer electrode 12 is made the ion collector. This may be accomplished simply by reversing the power supply connections to the two electrodes. Since the outer electrode 12 is now the ion collector, the radius of the annular opening 20 may be considerably reduced as shown in FIG. 1, thus providing a substantially smaller circumference. Since the same air-flow volume is desired through the opening 20, the annular width of the opening must be increased. This small circumference, large-width opening substantially reduces the turbulence of the incoming air flow, thus increasing measurement accuracy.

Using this type of arrangement, both the mobility and the ion density may be determined independently of each other. The ion mobility is determined from the location of the intersection points of the ion beam along the outer electrode 12. The ion density may be determined by measuring the magnitudes of the currents on the outer electrode 12.

To facilitate these measurements the outer electrode 12 may be formed by conductive segments 14 separated by insulators. Each of the segments 14 are intersected by ions having a particular mobility range. The higher the mobility (proportional to the velocity), the further the ion travels before it intersects an electrode segment 14. The current magnitude may be taken from each of the segments to provide an accurate measure of the ion density in that particular mobility range. Although only five segments 14 are shown, the whole length of the outer electrode 12 may be segmented. In view of this segmentation, in order to set up the proper electric field between the electrodes 10 and 12, the outer electrode should always function as the ground electrode while the center electrode is given either a positive or negative polarity.

Generally, the mobilities of the ions present in an air volume range over a wide spectrum of values. For a condenser chamber of a finite length with its electrodes energized at a particular voltage strength, the electric field created within the chamber may not be strong enough to pull some of the higher mobility ions down into an intersection with an electrode segment 14 while the ions are still within the chamber. Likewise, a very strong electric field might pull the low-mobility ions down into an intersection in such a fashion that there can be no discrimination between the different ions in this mobility range.

In order to alleviate this problem, a slowly varying d.c. voltage V is used at the power supply 16. This voltage variation is slow relative to the transit time of the ions in the device. Thus a complete set of measurements may be taken of the currents essentially at one voltage. The d.c. voltage waveform for the power supply 16 may, for example, be in the shape of an isosceles triangle formed either by smooth or stepped-ram functions. This type of slow voltage variation permits measurements to be taken of the mobilities of all ions present.

Figure 2:
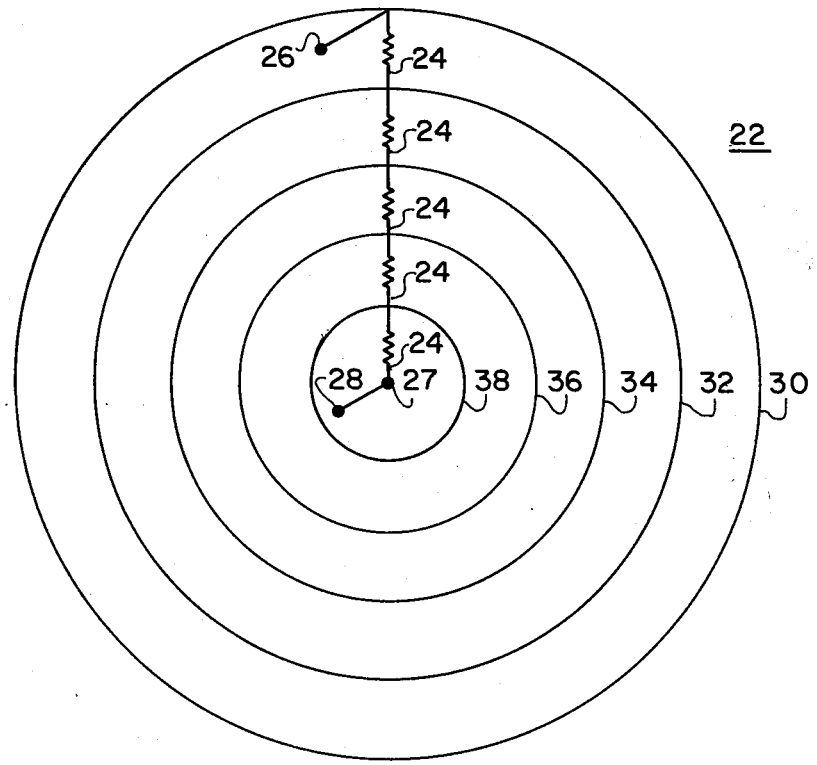
FIG. 2 is a schematic diagram of a wire array that may be used with the present invention to maintain a uniform electric field.

In order to obtain relatively accurate results, the electric field between the electrodes 10 and 12 must be uniform along the length of the electrodes. But at the ends of the electrode-formed chamber, the electric field lines tend to bulge out. In order to prevent this bulging and thus provide a completely uniform field, a set of annular wires 22 are located at both ends of the electrode chamber. FIG. 2 presents a schematic diagram of such a wire array 22 that may be used at the chamber ends. The outer annular wire 30 is connected to the outer electrode 12 via the lead 26. Thus they are at the same electric potential. Likewise, the inner point 27 is connected via the lead 28 to the center electrode 10 thus making point 27 and the electrode 10 the same electric potential. The resistors 24 provide the potential drop between the wire 30 potential and the point 27 potential. The annular wires 32, 34, 36, and 38 provide graduated equipotential circumferences between those two potential points 27 and 30. The electric field at the chamber ends is forced to conform to this electric field distribution thus providing a uniform field at the electrode ends.

In summary, the application of an essentially constant (slowly varying) electric field in a direction opposite to that of prior art "Gerdien Condensers" makes feasible the use of an entrance aperture near the center, rather than the outer, electrode. This allows a streamlining of the covering nose 18 of the device and allows a thin, small-circumference opening which results in a substantial turbulence reduction within the chamber. The use of a segmented collector electrode and a wire array for effecting an electric field uniformity within the chamber also add to the accuracy of the device.

This relatively simple configuration makes it possible to separate such important ionic species as $O^-$ and $O_2^-$. For example, the mobility resolution of this device for an aperture width of 0.5 cm, an outer electrode radius of 10 cm, with a 20 cm long outer electrode divided into a series of collectors each 0.5 cm in length is 8%.

Obviously, many modifications and variations of the present invention are possible in light of the above teachings. It is therefore to be understood that within the scope of the appended claims, the invention may be practiced otherwise than as specifically described.

What is claimed is:

1. A spectrometer for measuring the densities of charged particles in the atmosphere comprising:
   a cylindrical, center electrode having a small-radius;
   a cylindrical, outer electrode having a radius substantially larger than said center electrode and located concentrically around said center electrode to form a chamber;
   means for producing an electric field in said chamber radially between said center and outer electrodes such that the charged particles to be measured, upon entering said chamber, are attracted to said outer electrode; and
   means for covering one end of said chamber, said means containing an annular opening with a small radius relative to the radius of said outer electrode for providing a low-turbulence opening for the entrance of the charged particles to be measured.

2. A spectrometer for measuring the densities of charged particles in the atmosphere comprising:

cylindrical, center electrode means having a small radius;

cylindrical, outer electrode means having a radius substantially larger than said center electrode and located concentrically around said center electrode to form a chamber;

electric field-producing means for setting up an electric field in said chamber radially between said center and outer electrode means such that the charged particles to be measured, upon entering said chamber, are attracted to said outer electrode means;

means for covering one end of said chamber, said means containing an annular opening with a small radius relative to the radius of said outer electrode means for providing a low-turbulence opening for the entrance of the charged particles to be measured; and an array of conductors positioned at the ends of said chamber, each conductor being energized with a different electric potential for keeping the electric field at the ends of said center and outer electrode means uniform with respect to the field, within said chamber.

3. A spectrometer as defined in claim 2, wherein said covering means is in the shape of a cone.

4. A spectrometer as defined in claim 2, wherein said electric field-producing means comprises a voltage supply with its voltage varying in a sawtooth fashion slowly with respect to the charged particle transit times through said chamber, connected across said center and said outer electrode means so that an electric field is set up between the two electrode means.

5. A spectrometer as defined in claim 2, wherein said outer electrode means is formed by a plurality of conductor segments separated by insulating means.

6. A spectrometer as defined by claim 2 wherein said conductor arrays comprise:

outer annular conductor means having radius approximately the radius of said outer electrode means at the same electric potential as said outer electrode means and adjacent to it;

center conductor means at the same electric potential as said center electrode means and adjacent to it;

a plurality of resistor means making a series connection between said outer conductor and said inner conductor for providing a potential drop between said conductors; and a plurality of annular conductor means with radii graduated so that they form a series of concentric conductors between said outer conductor means and said inner conductor means, each concentric conductor being connected to a different point in the series connection formed by said plurality of resistor means so that they form graduated equipotential circumferences between said inner and said outer conductor potentials.

* * * * *